United States Patent
Jacobson et al.

(10) Patent No.: US 7,041,625 B2
(45) Date of Patent: May 9, 2006

(54) METHOD TO INHIBIT ETHYLENE RESPONSES IN PLANTS

(75) Inventors: Richard Martin Jacobson, Chalfont, PA (US); Martha Jean Kelly, Collegeville, PA (US); Fiona Linette Wehmeyer, Roslyn, PA (US); Edward C. Sisler, Raleigh, NC (US)

(73) Assignee: Rohm and Haas Company, Philadelphia, PA (US)

( * ) Notice: Subject to any disclaimer, the term of this patent is extended or adjusted under 35 U.S.C. 154(b) by 389 days.

(21) Appl. No.: 10/645,769

(22) Filed: Aug. 21, 2003

(65) Prior Publication Data

US 2005/0043179 A1   Feb. 24, 2005

(51) Int. Cl.
*A01N 27/00* (2006.01)
*A01N 43/00* (2006.01)

(52) U.S. Cl. .................. 504/193; 504/195; 504/218; 504/235; 504/236; 504/240; 504/246; 504/276; 504/281; 504/284; 504/289; 504/298; 504/309; 504/346; 504/348; 504/353; 504/356; 504/357

(58) Field of Classification Search ............. 504/193, 504/195, 218, 235, 236, 240, 246, 276, 281, 504/284, 289, 298, 309, 346, 348, 353, 356, 504/357
See application file for complete search history.

(56) References Cited

U.S. PATENT DOCUMENTS

| 5,100,462 | A | 3/1992 | Sisler et al. ............. 71/121 |
| 5,518,988 | A | 5/1996 | Sisler et al. ............. 504/114 |
| 6,017,849 | A | 1/2000 | Daly et al. .............. 504/114 |
| 6,313,068 | B1 | 11/2001 | Daly et al. ............. 504/114 |
| 6,365,549 | B1 | 4/2002 | Sisler ................... 504/114 |
| 6,452,060 | B1 | 9/2002 | Jacobson ............... 585/638 |

FOREIGN PATENT DOCUMENTS

WO   WO 02/067678   9/2002
WO   WO 02/068367   9/2002

OTHER PUBLICATIONS

Sisler et al. "Inhibitors of ethylene responses in plants at teh receptor level: Recent developments". Physiologia Plantarum. 100(3):577-582. 1997.*

Mark S. Baird, et al., The Preparation and Lithiation of 1-Halogenocyclopropenes, J. Chem. Soc. Perkin Trans. vol. 1 PP 1845-1853 (1986).

* cited by examiner

*Primary Examiner*—S. Mark Clardy
(74) *Attorney, Agent, or Firm*—Thomas D. Rogerson

(57) ABSTRACT

The present invention generally relates to methods of inhibiting ethylene responses in plants and plant materials, and particularly relates to methods of inhibiting various ethylene responses including plant maturation and degradation, by exposing plants to cyclopropene derivatives and compositions thereof wherein the cyclopropene is associated with another ring system.

12 Claims, No Drawings

METHOD TO INHIBIT ETHYLENE RESPONSES IN PLANTS

CROSS REFERENCE TO RELATED PATENT APPLICATIONS

This is a non-provisional application of prior now abandoned U.S. provisional application Ser. No. 60/271,533 filed Feb. 26, 2001 and PCT/US02/08160 filed on Feb. 25, 2002.

The present invention generally relates to methods of inhibiting ethylene responses in plants and plant materials, and particularly relates to methods of inhibiting various ethylene responses including plant maturation and degradation, by exposing plants to cyclopropene derivatives and compositions thereof wherein the cyclopropene is associated with another ring system.

It is well known that ethylene can cause the premature death of plants or plant parts including, for example, flowers, leaves, fruits, and vegetables. Ethylene also promotes leaf yellowing and stunted growth as well as premature fruit, flower, and leaf drop. Such activities are understood to be achieved through interaction with a specific ethylene receptor in the plant. Many compounds other than ethylene interact with this receptor: some mimic the action of ethylene; others prevent ethylene from binding and thereby counteract its action. To address these ethylene-induced effects, very active and intense research presently concerns the investigation of ways to prevent or reduce the deleterious effects of ethylene on plants.

Methods of combating the ethylene response in plants with diazocyclopentadiene and derivatives thereof are disclosed in U.S. Pat. No. 5,100,462 to Sisler et al. U.S. Pat. No. 5,518,988 to Sisler et al. discloses the use of cyclopropene and its derivatives, including 1-methylcyclopropene, as effective blocking agents for ethylene binding. However, a major problem with these compounds is that they are typically unstable gases which present explosive hazards when compressed.

Notwithstanding these efforts, there still remains a need in the art for compounds and compositions which will control plant maturation and degradation. Preferably, the new compounds will avoid the explosive hazards of 1-methylcyclopropene and, in addition, provide alternative means of delivery, such as through liquid or solid formulations.

We have discovered a new class of cyclopropene derivatives which provide many of the advantages noted above. These compounds, and their compositions, provide a method of inhibiting an ethylene response in a plant comprising the step of contacting the plant with an effective ethylene response-inhibiting amount of a cyclopropene derivative of formula I or II:

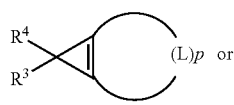

I

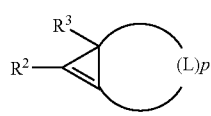

II or a mixture thereof, wherein:

a) each $R^2$, $R^3$, and $R^4$ is independently a group of the formula:

-(L)$_n$-Z wherein:
i) n is an integer from 0 to 12 and p is an integer from 3 to 10;
ii) each L is independently selected from a member of the group D, E, or J wherein:
D is of the formula:

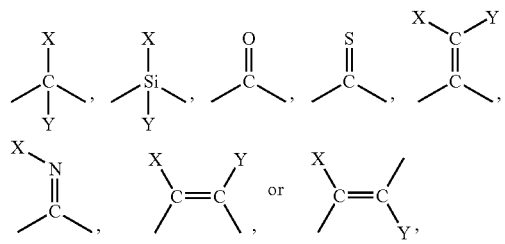

E is of the formula:

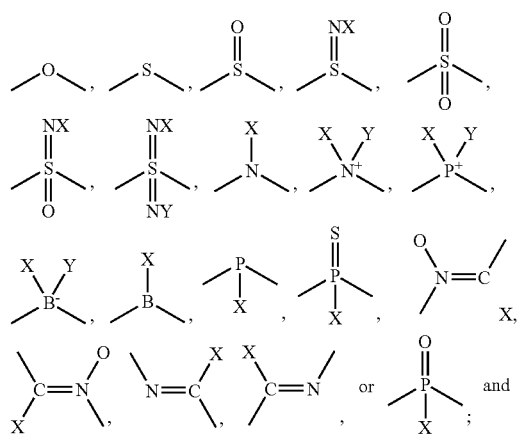

J is of the formula:

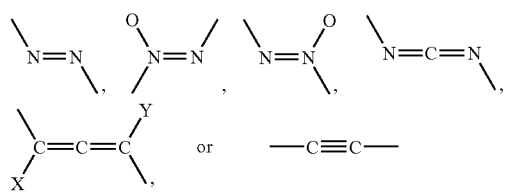

wherein:
A) each X and Y is independently a group of the formula:

-(L)m-Z;

and
B) m is an integer from 0 to 8; and
C) no more than two E groups are adjacent to each other and no J groups are adjacent to each other;
iii) each Z is independently selected from:
A) hydrogen, halo, cyano, nitro, nitroso, azido, chlorate, bromate, iodate, isocyanato, isocyanido, isothiocyanato, pentafluorothio, or B) a group G, wherein G is an unsubstituted or substituted; unsaturated, partially saturated, or saturated; monocyclic, bicyclic, tricyclic, or fused; carbocyclic or heterocyclic ring system wherein;
1) when the ring system contains a 3 or 4 membered heterocyclic ring, the heterocyclic ring contains 1 heteroatom;
2) when the ring system contains a 5, or more membered heterocyclic ring or a polycyclic heterocyclic ring, the heterocyclic or polycyclic heterocyclic ring contains from 1 to 4 heteroatoms;
3) each heteroatom is independently selected from N, O, and S;
4) the number of substituents is from 0 to 5 and each substituent is independently selected from X
b) the total number of non-hydrogen atoms in each compound is 50 or less;

its enantiomers, stereoisomers, salts, and mixtures thereof; or a composition thereof.

Another embodiment of this invention is a method of inhibiting an ethylene response in a plant, comprising contacting the plant with an effective ethylene response-inhibiting amount of a compound of formula III:

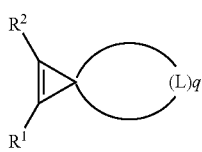

III wherein:
a) each $R^1$ and $R^2$ is independently a group of the formula:

-(L)$_n$-Z wherein:
i) n is an integer from 0 to 12 and q is an integer from 2 to 11;
ii) L, Z, D, E, J, X, and Y are as defined above;
iii) no more than two E groups are adjacent to each other and no J groups are adjacent to each other; and
b) the total number of non-hydrogen atoms in each compound is 50 or less;

its enantiomers, stereoisomers, salts, and mixtures thereof; or a composition thereof.

For the purposes of this invention, in the structural representations of the various L groups each open bond indicates a bond to another L group, a Z group, or the cyclopropene moiety. For example, the structural representation

indicates an oxygen atom with bonds to two other atoms; it does not represent a dimethyl ether moiety.

Typical $R^1$, $R^2$, $R^3$, and $R^4$ groups include, for example: alkenyl, alkyl, alkynyl, acetylaminoalkenyl, acetylaminoalkyl, acetylaminoalkynyl, alkenoxy, alkoxy, alkynoxy, alkoxyalkoxyalkyl, alkoxyalkenyl, alkoxyalkyl, alkoxyalkynyl, alkoxycarbonylalkenyl, alkoxycarbonylalkyl, alkoxycarbonylalkynyl, alkylcarbonyl, alkylcarbonyloxyalkyl, alkyl(alkoxyimino)alkyl, carboxyalkenyl, carboxyalkyl, carboxyalkynyl, dialkylamino, haloalkoxyalkenyl, haloalkoxyalkyl, haloalkoxyalkynyl, haloalkenyl, haloalkyl, haloalkynyl, hydroxyalkenyl, hydroxyalkyl, hydroxyalkynyl, trialkylsilylalkenyl, trialkylsilylalkyl, trialkylsilylalkynyl, dialkylphosphonato, dialkylphosphato, dialkylthiophosphato, dialkylaminoalkyl, alkylsulfonylalkyl, alkylthioalkenyl, alkylthioalkyl, alkylthioalkynyl, dialkylaminosulfonyl, haloalkylthioalkenyl, haloalkylthioalkyl, haloalkylthioalkynyl, alkoxycarbonyloxy; cycloalkenyl, cycloalkyl, cycloalkynyl, acetylaminocycloalkenyl, acetylaminocycloalkyl, acetylaminocycloalkynyl, cycloalkenoxy, cycloalkoxy, cycloalkynoxy, alkoxyalkoxycycloalkyl, alkoxycycloalkenyl, alkoxycycloalkyl, alkoxycycloalkynyl, alkoxycarbonylcycloalkenyl, alkoxycarbonylcycloalkyl, alkoxycarbonylcycloalkynyl, cycloalkylcarbonyl, alkylcarbonyloxycycloalkyl, carboxycycloalkenyl, carboxycycloalkyl, carboxycycloalkynyl, dicycloalkylamino, halocycloalkoxycycloalkenyl, halocycloalkoxycycloalkyl, halocycloalkoxycycloalkynyl, halocycloalkenyl, halocycloalkyl, halocycloalkynyl, hydroxycycloalkenyl, hydroxycycloalkyl, hydroxycycloalkynyl, trialkylsilylcycloalkenyl, trialkylsilylcycloalkyl, trialkylsilylcycloalkynyl, dialkylaminocycloalkyl, alkylsulfonylcycloalkyl, cycloalkylcarbonyloxyalkyl, cycloalkylsulfonylalkyl, alkylthiocycloalkenyl, alkylthiocycloalkyl, alkylthiocycloalkynyl, dicycloalkylaminosulfonyl, haloalkylthiocycloalkenyl, haloalkylthiocycloalkyl, haloalkylthiocycloalkynyl; aryl, alkenylaryl, alkylaryl, alkynylaryl, acetylaminoaryl, aryloxy, alkoxyalkoxyaryl, alkoxyaryl, alkoxycarbonylaryl, arylcarbonyl, alkylcarbonyloxyaryl, carboxyaryl, diarylamino, haloalkoxyaryl, haloaryl, hydroxyaryl, trialkylsilylaryl, dialkylaminoaryl, alkylsulfonylaryl, arylsulfonylalkyl, alkylthioaryl, arylthioalkyl, diarylaminosulfonyl, haloalkylthioaryl; heteroaryl, alkenylheteroaryl, alkylheteroaryl, alkynylheteroaryl, acetylaminoheteroaryl, heteroaryloxy, alkoxyalkoxyheteroaryl, alkoxyheteroaryl, alkoxycarbonylheteroaryl, heteroarylcarbonyl, alkylcarbonyloxyheteroaryl, carboxyheteroaryl, diheteroarylamino, haloalkoxyheteroaryl, haloheteroaryl, hydroxyheteroaryl, trialkylsilylheteroaryl, dialkylaminoheteroaryl, alkylsulfonylheteroaryl, heteroarylsulfonylalkyl, alkylthioheteroaryl, heteroarylthioalkyl, diheteroarylaminosulfonyl, haloalkylthioheteroaryl; heterocyclyl, alkenylheteroycycyl, alkylheteroycycyl, alkynylheteroycycyl, acetylaminoheterocyclyl, heterocyclyloxy, alkoxyalkoxyheterocyclo, alkoxyheterocyclyl, alkoxycarbonylheterocyclyl, heterocyclylcarbonyl, alkylcarbonyloxyheterocyclyl, carboxyheterocyclyl, diheterocyclylamino, haloalkoxyheterocyclyl, haloheterocyclyl, hydroxyheterocyclyl, trialkylsilylheterocyclyl, dialkylaminoheterocyclyl, alkylsulfonylheterocyclyl, alkylthioheterocyclyl, heterocyclylthioalkyl, diheterocyclylaminosulfonyl, haloalkyllthioheterocyclyl; hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

Typical G groups include, for example: saturated or unsaturated cycloalkyl, bicyclic, tricyclic, polycyclic, saturated or unsaturated heterocyclic, unsubstituted or substituted phenyl, naphthyl, or heteroaryl ring systems such as, for example, cyclopropyl, cyclobutyl, cyclopent-3-en-1-yl, 3-methoxycyclohexan-1-yl, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, 2-iodo-4-methylphenyl, pyridin-2-yl, pyridin-3-yl, pyridin-4-yl, pyrazinyl, pyrimidin-2-yl, pyrimidin-4-yl, pyrimidin-5-yl, pyridazinyl, triazol-1-yl, imidazol-1-yl, thiophen-2-yl, thiophen-3-yl, furan-2-yl, furan-3-yl, pyrrolyl, oxazolyl, isoxazolyl, thiazolyl, isothiazolyl, oxadiazolyl, thiadiazolyl, quinolyl, isoquinolyl, tetrahydrofuryl, pyrrolidinyl, piperidinyl, tetrahydropyranyl, morpholinyl, piperazinyl, dioxolanyl, dioxanyl, indolinyl and 5-methyl-6-chromanyl, adamantyl, norbornyl, and their substituted analogs such as, for example: 3-butyl-pyridin-2-yl, 4-bromo-pyridin-2-yl, 5-carboethoxy-pyridin-2-yl, 6-methoxyethoxy-pyridin-2-yl, When the compound is of formula I; preferably, one of $R^3$ and $R^4$ is hydrogen; more preferably, both R3 and $R^4$ are hydrogen. When the compound is of formula II; preferably one of $R^2$ and $R^3$ is hydrogen; more preferably $R^3$ is hydrogen; most preferably, both $R^2$ and $R^3$ are hydrogen. When the compound is of formula III; preferably one of $R^1$ and $R^2$ is hydrogen; more preferably, both $R^1$ and $R^2$ are hydrogen.

Preferably, n is from 0 to 8. Most preferably, n is from 1 to 7. Preferably, m is 0 to 4. Most preferably, m is from 0 to 2. Preferably, p is from 4 to 8. Most preferably, p is from 4 to 7. Preferably, q is from 2 to 8. More preferably, q is from 3 to 7. Most preferably, q is from 4 to 6.

Preferably, D is —CXY—, —SiXY—, —CO—, or —CS—. More preferably D is —CO— or —CXY—. Preferably, E is —O—, —S—, —NX—, or —SO$_2$—. More preferably, E is —O—. Preferably, X and Y are independently H, halo, OH, SH, —C(O)(C$_1$–C$_4$)alkyl-, —C(O)O (C$_1$–C$_4$)alkyl-, —O—(C$_1$–C$_4$)alkyl, —S—(C$_1$–C$_4$)alkyl, or substituted or unsubstituted (C$_1$–C$_4$)alkyl. Preferably, Z is H, halo, or G. More preferably, Z is H or G.

Preferably, each G is independently a substituted or unsubstituted; five, six, or seven membered; aryl, heteroaryl, heterocyclic, or cycloalkyl ring. More preferably, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Even more preferably, G is unsubstituted or substituted phenyl, cyclopentyl, cycloheptyl, or cyclohexyl. Most preferably, G is cyclopentyl, cycloheptyl, cyclohexyl, phenyl, or substituted phenyl wherein the substituents are independently selected from 1 to 3 of methyl, methoxy, and halo.

Another aspect of the present invention is a method of blocking ethylene receptors in plants by applying to the plants an effective ethylene receptor-blocking amount of the cyclopropene derivative of formula I, II, or III, or a composition thereof.

Also disclosed are methods of inhibiting abscission in a plant, prolonging the life of a cut flower, and inhibiting the ripening of a picked fruit or vegetable, comprising applying to the plant an effective amount of the cyclopropene derivative of formula I, II, or III, or a composition thereof.

The methods described herein may be carried out in a variety of ways, such as by contacting the plant with a cyclopropene derivative or a composition thereof, whether in solid, liquid, or gaseous form, or by exposing the plant, cut flower, picked fruit or picked vegetable into an atmosphere infused with the cyclopropene derivative or a composition thereof. These and other suitable methods of application are discussed in detail below. For the purposes of this invention, "contacting" means to bring the cyclopropene and a plant into intimate association with each other such that a sufficient number of ethylene receptors are effected by the cyclopropene.

Agricultural compositions comprising the compounds of this invention are also encompassed by the invention. Preferably the compositions comprise 0.005% to 99%, by weight; preferably 1% to 95%, by weight; more preferably 2% to 90%, by weight; even more preferably 3% to 80%, by weight; or most preferably 4% to 70%, by weight, of the active compounds of the present invention. These compositions may comprise one or more adjuvants, such as, for example, carriers, extenders, binders, lubricants, surfactants and/or dispersants, wetting agents, spreading agents, dispersing agents, stickers, adhesives, defoamers, thickeners, and emulsifying agents. Such adjuvants commonly used in the art can be found in the John W. McCutcheon, Inc. publication *Detergents and Emulsifiers, Annual*, Allured Publishing Company, Ridgewood, N.J., U.S.A.

As used herein, all percentages are percent by weight and all parts are parts by weight, unless otherwise specified, and are inclusive and combinable. All ratios are by weight and all ratio ranges are inclusive and combinable. All molar ranges are inclusive and combinable.

Numerous organic solvents may be used as carriers for the active compounds of the present invention such as, for example, hydrocarbons such as hexane, benzene, toluene, xylene, kerosene, diesel oil, fuel oil and petroleum naphtha, ketones such as acetone, methyl ethyl ketone and cyclohexanone, chlorinated hydrocarbons such as carbon tetrachloride, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine.

Mixtures of water and organic solvents, either as solutions or emulsions, can also be employed as inert carriers for the active compounds.

Solid, liquid, and gaseous formulations can be prepared by various conventional procedures. Thus, the active ingredient, in finely divided form if a solid, may be tumbled together with finely divided solid carrier. Alternatively, the active ingredient in liquid form, including mixtures, solutions, dispersions, emulsions and suspensions thereof, may be admixed with a solid carrier in finely divided form. Furthermore, the active ingredient in solid form may be admixed with a liquid carrier to form a mixture, solution, dispersion, emulsion, suspension or the like.

The active compounds of the present invention can be applied to plants by various suitable means. For example, an active compound may be applied alone in gaseous, liquid, or solid form by contacting the compound with the plant to be treated. Additionally the active compound may be converted to the salt form, and then applied to the plants. Alternatively, compositions containing one or more active compounds of the present invention may be formed. The compositions may be applied in gaseous, liquid, or solid form by contacting the composition with the plant to be treated. Such compositions may include an inert carrier. Similarly, when in gaseous form, the compound may be dispersed in an inert gaseous carrier to provide a gaseous solution. The active compound may also be suspended in a liquid solution such as an organic solvent or an aqueous solution that may serve as the inert carrier. Solutions containing the active compound may be heterogeneous or homogeneous and may be of various forms including mixtures, dispersions, emulsions, suspensions and the like.

The cyclopropenes may also be encapsulated into a molecular encapsulation agent. Preferred encapsulating agents include cyclodextrins, crown ethers, polysiloxanes, and zeolites. More preferred encapsulating agents include α-cyclodextrin, β-cyclodextrin, and γ-cyclodextrin. The most preferred encapsulating agent will vary depending upon the size of the R substituents. However, as one skilled in the art will appreciate, any cyclodextrin or mixture of cyclodextrins, cyclodextrin polymers as well as modified cyclodextrins can also be utilized pursuant to the present invention. Cyclodextrins are available from Wacker Biochem Inc., Adrian, Mich. or Cerestar USA, Hammond, Ind., as well as other vendors.

The active compounds and compositions thereof can also be applied as aerosols, e.g., by dispersing them in air using a compressed gas such as, for example, nitrogen, carbon dioxide, dichlorodifluoromethane, trichlorofluoromethane, or other halocarbons.

The amount of the cyclopropene needed to inhibit ethylene effects will vary depending upon the particular cyclopropene, the type and amount of plant material present, the cyclopropene composition used, and the volume to be treated. Generally, a gas treatment (measured volume/volume) concentration of the cyclopropene in the treated chamber of from about 0.1 part per billion ("ppb") to 1000 parts per million ("ppm") provides adequate ethylene inhibition. Likewise, an applied spray treatment (measured weight/weight) concentration of the cyclopropene of from about 0.01 part per billion ("ppb") to 1000 parts per million ("ppm") provides adequate ethylene inhibition.

The term "plant" is used in a generic sense herein, and includes, for example, woody-stemmed plants such as trees and shrubs; herbs; vegetables, fruits, and agricultural crops; and ornamental plants. Plants to be treated by the methods described herein include whole plants and any portions thereof, such as field crops, potted plants, seeds, cut flowers (stems and flowers), and harvested fruits and vegetables.

Plants treated with the compounds and by the methods of the present invention are preferably treated with a non-phytotoxic amount of the active compound.

The present invention can be employed to modify a variety of different ethylene responses such as, for example, the ripening and/or senescence of flowers, fruits, and vegetables; abscission of foliage, flowers, and fruit; the shortening of life of ornamentals such as potted plants, cut flowers, shrubbery, seeds, and dormant seedlings; in some plants (e.g., pea) the inhibition of growth, the stimulation of growth (e.g., rice), auxin activity, inhibition of terminal growth, control of apical dominance, increase in branching, increase in tillering, changing the morphology of plants, modifying the susceptibility to plant pathogens such as fungi, changing bio-chemical compositions of plants (such as increasing leaf area relative to stem area), abortion or inhibition of flowering and seed development, lodging effects, stimulation of seed germination and breaking of dormancy, and hormone or epinasty effects.

Active compounds of the present invention have proven to be unexpectedly potent inhibitors of ethylene action on plants, fruits and vegetables, even when applied at low concentrations. Among other things, compounds of the present invention may result in a longer period of insensitivity to ethylene than compounds found in the prior art. This longer period of insensitivity may occur even when compounds of the present invention are applied at a lower concentration than previous compounds.

The compounds of this invention can be prepared by a number of methods. For general references see Closs, G. L. *Advan. Alicyclic Chem.* 1966, 1, 53–127 and Al Dulayymi, A. R.; Al Dulayymi, J. R; Baird, M. S.; and Koza, G. *Russian Journal of Organic Chemistry* 1997, 33, 798–816.

The reaction of a bromo-olefin with dibromocarbene gives a tribromocyclopropane, which can be converted to the cyclopropene with methyllithium or other organolithium compounds as shown. (see Baird, M. S.; Hussain, H. H.; Nethercott, W. J. *Chem. Soc. Perkin Trans.* 1 1986, 1845–1854 and Baird, M. S.; Fitton, H. L.; Clegg, W; McCamley, A. *J. Chem. Soc. Perkin Trans.* 1 1993, 321–326). If one equivalent of methyllithium or other alkyllithium is used, the mono-brominated cyclopropene is obtained. With two or more equivalents of the alkyllithium, the lithiated cyclopropene is formed. This can be quenched with water to give the cyclopropenes shown (E=H). Alternatively, the cyclopropenyllithium can be reacted with electrophiles to give derivatived cyclopropenes. Examples of such electrophiles include alkylating agents, trisubstituted chlorosilanes, borates, dialkyl or diaryl disulfides, ketones, aldehydes, esters, amides and nitriles.

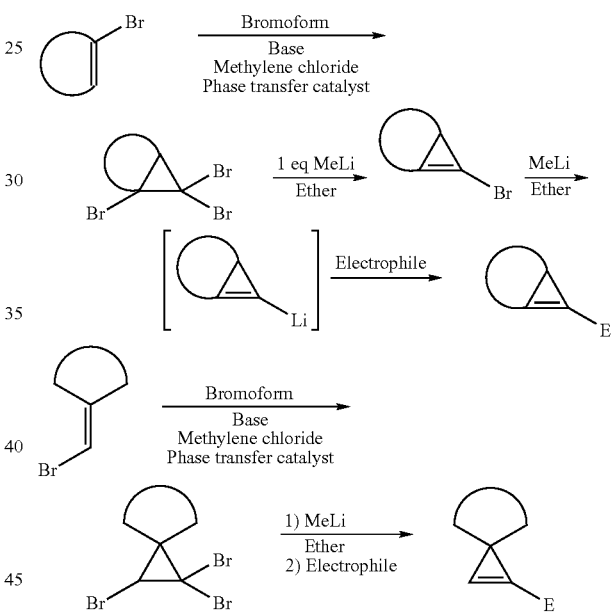

The bromo-olefins can be prepared by standard methods. Chloro-olefins can be used in place of bromo-olefins.

The tribrominated cyclopropanes can also be converted to mono-brominated cyclopropanes with reducing agents such as diethylphosphite. Other reducing agents could be used.

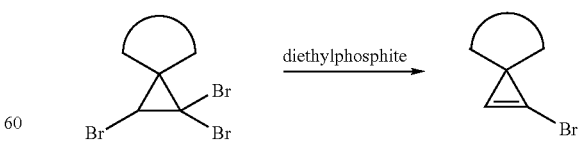

A 1,1-disubstituted olefin can also react with dibromocarbene to give a dibrominated intermediate. This can be reduced with zinc to the mono-brominated cyclopropane. Elimination of the bromide with base gives the cyclopropene (reference Binger, P. *Synthesis* 1974, 190).

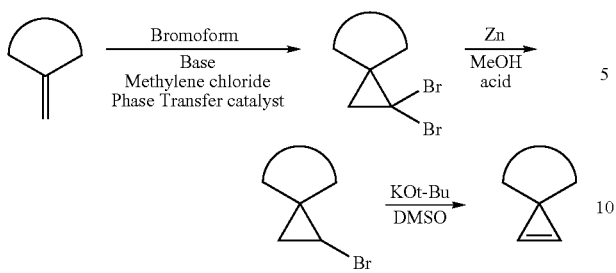

Substituted cyclopropenes can be deprotonated with alkyllithium reagents and reacted with electrophiles.

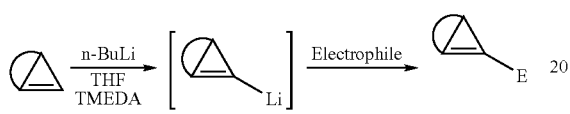

Tribromocyclopropanes or cyclopropenes containing an alcohol can be converted to a good leaving group such as a sulfonate derivative. The leaving group can be displaced with nucleophiles to give other substituted cyclopropenes.

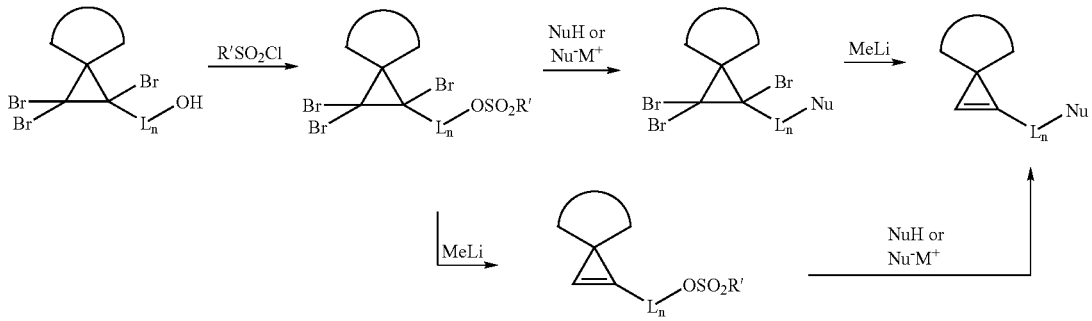

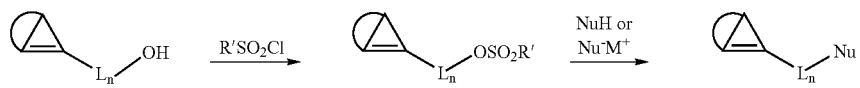

1-Trialkylsilyl-2-halocyclopropanes also undergo a fluoride catalyzed elimination to give cyclopropenes (Billups, W. E.; Lee, G-A; Arney, B. E.; Whitmire, K. H. *J. Am. Chem. Soc.*, 1991, 113, 7980. and Banwell, M. G.; Corbett, M.; Gulbis, J.; Mackay, M. F.; Reum, M. E. *J. Chem. Soc. Perkin Trans.* 1, 1993, 945).

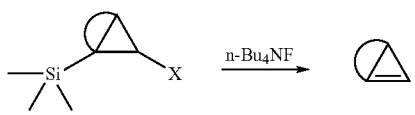

Spirocyclic ketals can be prepared by the method of Isaka, M.; Matsuzawa, S. Y.; Ejiri, S.; Miyachi, Y.; Nakamura, E. *J. Org. Chem.*, 1989, 54, 4727.

Other methods for making cyclopropenes can be found in the following references: Duerr, H., *Angew. Chem.* 1967, 24, 1104; Closs et al., *J. Am. Chem.* 1963, 85, 3796; Baird, M. S.; Dale, C. M.; Al Dulayymi, J. R. *J. Chem. Soc. Perkin Trans.* 1, 1993, 1373–1374; Köster, R. et al., *Liebigs Annalen Chem.* 1973, 1219–1235; Closs, G. L.; Closs, L. E., *J. Am. Chem. Soc.*, 1961, 83, 1003–1004; Stoll, A. T.; Negishi, E., *Tetrahedron Lett.* 1985, 26, 5671–5674.

EXAMPLES

General: Compound 1 was stored at −80° C. All reactions were carried out under an atmosphere of nitrogen. All target compounds were 80% or greater purity unless otherwise noted.

Example 1

Preparation of Bicyclo[5.1.0]oct-1(8)-ene (Compound 1)

a. 1,2-Dibromocycloheptane

To a cooled solution of 10.02 g (0.104 mol) of cycloheptene in 60 g of methylene chloride was added 15.99 g (0.0999 mol) of bromine in methylene chloride at a rate to keep the internal temperature at −20° C. to −25° C. Solvent was removed from the reaction mixture in vacuo to yield 23.4 g of 1,2-dibromoheptane.

b. 1-Bromo-cycloheptene

To 6.2 g (11.1 mmol) of a solution of 20% (w/w) potassium tert-butoxide in tetrahydrofuran was added 2.3 g (8.98 mmol) of 1,2-dibromoheptane. After stirring 40 minutes the reaction mixture was concentrated in vacuo. After adding diethyl ether and water, the resulting mixture was transferred to a separatory funnel. The isolated organic layer was dried over magnesium sulfate and filtered. The filtrate was concentrated in vacuo to yield 1.5 g of 1-bromo-cycloheptene.

c. N,N'-dibenzyl-N,N,N',N'-tetramethylethylenediammonium dibromide and N,N'-dibenzyl-N,N,N',N'-tetraethylethylenediammonium dibromide (Phase transfer catalysts).

To a stirred solution of 16.5 g (142 mmol) of N,N,N',N'-tetramethylethylenediamine in 60 g of acetonitrile was added 50.1 g (292 mmol) of benzyl bromide. The mixture self warmed and was allowed to stir for 2.5 hours whereon a heavy precipitate was observed. The slurry was diluted with diethyl ether, filtered, washed with diethyl ether and dried yielding 61.8 g of the desired N,N'-dibenzyl-N,N,N',N'-tetramethylethylenediammonium dibromide, a white solid mp 230–232° C.

In an analogous way, using N,N,N',N'-tetraethylethylenediamine one obtains N,N'-dibenzyl-N,N,N',N'-tetraethylethylenediammonium dibromide, a white solid mp 190–193° C., decomposes.

d. 1,8,8-Tribromo-bicyclo[5.1.0]octane

To a solution of 12 g (6.86 mmol) of 1-bromo-cycloheptene in 52 g (206 mmol) of bromoform and 56 g of methylene chloride was added 0.73 g (1.59 mmol) of N,N'-dibenzyl-N,N,N',N'-tetramethylethylenediammonium dibromide and 18.8 g (152 mmol) of 45% aqueous potassium hydroxide. After 24 hours the reaction mixture was poured onto water. The resulting mixture was transferred to a separatory funnel and the phases were separated. To the isolated organic layer was added 0.73 g (1.59 mmol) of N,N'-dibenzyl-N,N,N',N'-tetramethylethylenediammonium dibromide and 18.8 g (152 mmol) 45% aqueous potassium hydroxide. After 24 hours the reaction mixture was poured onto water. The resulting mixture was transferred to a separatory funnel and the phases were separated. The isolated organic layer was dried over magnesium sulfate and filtered. The filtrate was dried in vacuo. The residue obtained was purified by column chromatography with hexanes. The resulting oil was purified by vacuum distillation to yield 7.8 g of 1,8,8-tribromo-bicyclo[5.1.0]octane.

e. Bicyclo[5.1.0]oct-1(8)-ene

A solution of 1.06 g (3.05 mmol) of 1,8,8-tribromo-bicyclo[5.1.0]octane in 4 ml of diethyl ether was placed under a nitrogen atmosphere via use of a Firestone valve. While cooling in an ice water bath, 6.55 ml (9.15 mmol) of 1.4M methyl lithium in diethyl ether was added slowly by syringe. After 15 minutes, 2 ml of water was added via syringe. The resulting mixture was transferred to a separatory funnel and the phases were separated. The organic layer was dried over $MgSO_4$ and filtered. The solvent was removed from the filtrate in vacuo with a bath temperature under 20° C. to yield 0.370 g of bicyclo[5.1.0]oct-1(8)-ene 30% pure as an oil.

Example 2

Preparation of
6.6-Dimethyl-1-octyl-4.8-dioxa-spiro[2.5]oct-1-ene
(Compound 2)

This compound is prepared by the method of Isaka, M.; Matsuzawa, S. Y.; Ejiri, S.; Miyachi, Y.; Nakamura, E. *J. Org. Chem.*, 1989, 54, 4727.

The compounds were characterized using a variety of spectroscopic techniques. The NMR data for the compounds is given in Table 1. For compounds containing impurities, the chemical shifts of the impurities are not reported, and the integrals are adjusted to reflect only the contribution of the target compound.

TABLE 1

NMR Data

| Cmpd # | NMR |
|---|---|
| 1 | (CDCl3): 1.3–2.8(m, 11H), 6.5(s, 1H) |
| 2 | (CDCl3): 0.87(t, 3H), 1.00(s, 3H), 1.06(s, 3H), 1.15–1.45 (m, 10H), 1.6(pentet, 2H), 2.52(t, 2H), 3.65–3.8(m, 4H), 7.32(bs, 1H) |

Biological Activity:

Tomato Epinasty Test

Objective: The test procedure is designed to determine the ability of an experimental compound to block the epinastic growth response induced by ethylene in tomato plants when the experimental compound is administered either as a volatile gas or as a component of a spray solution.

Treatment chambers are of an appropriate size for the test plants and are airtight. Each is fitted with a reusable septum to be used for injection of ethylene. Test plants are Patio variety tomato seedlings planted two plants per three inch square plastic pot.

Volatile gas treatment entails placing two pots of Patio var. tomatoes into a polystyrene 4.8 L volume treatment chamber along with one-half (upper or lower section) of a 50×9 mm plastic Petri dish containing a Gelman filter pad. The appropriate amount of experimental compound, dissolved in 1.0 ml acetone, is pipetted onto the filter pad and the chamber immediately sealed. Four hours later ethylene gas equal to 10 ppm v/v final concentration is injected into the sealed chamber. Sixteen hours later the chambers are opened in an exhaust hood, allowed to air and the plants scored visually for the degree of protection against ethylene-induced epinasty conferred by the experimental compound when compared to ethylene treated and untreated controls on a scale of 0 to 10. A rating of 10 means complete protection. A rating of 0 means no protection from the effects of ethylene. Gas treatment concentrations are volume/volume.

Spray application treatment entails using a DeVilbiss atomizer to completely cover all foliage and stems of two pots of Patio var. tomato plants with the appropriate amount of experimental compound dissolved in 10% acetone/90% water with 0.05% Silwett L-77 surfactant. Plants are air-dried in a drying hood for four hours then transferred to a 4.8 L polystyrene chamber which is sealed.

Ethylene gas equal to 10 ppm v/v final concentration is injected into the sealed chamber. Sixteen hours later the chambers are opened in an exhaust hood, allowed to air and the plants scored visually for the degree of protection against ethylene-induced epinasty conferred by the experimental compound when compared to ethylene treated and untreated controls on a scale of 0 to 10. A rating of 10 means complete protection. A rating of 0 means no protection from the effects of ethylene.

The activity of the compounds of this invention in the tomato epinasty test when applied as a gas or as a spray is given in Table 2.

TABLE 2

Activity of the compounds of this invention in the tomato epinasty test.

| Cmpd# | Gas @ 1000 ppm | Gas @ 10 ppm | Spray @ 10 ppm |
|---|---|---|---|
| 1 | NT | 8 | 0 |
| 2 | 4 | 0 | 0 |

NT means not tested.

We claim:

1. A method of inhibiting an ethylene response in a plant comprising the step of contacting the plant with an effective ethylene response-inhibiting amount of a cyclopropene derivative of formula I or II:

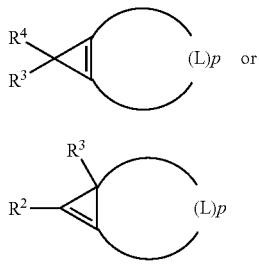

or a mixture thereof, wherein:

a) each $R^2$, $R^3$, and $R^4$ is independently a group of the formula:

-(L)$_n$-Z wherein:
i) n is an integer from 0 to 12 and p is an integer from 3 to 10;
ii) each L is independently selected from a member of group D, E, or J wherein:
D is of the formula:

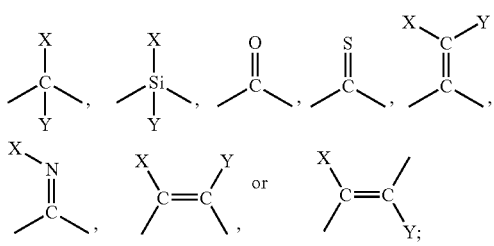

E is of the formula:

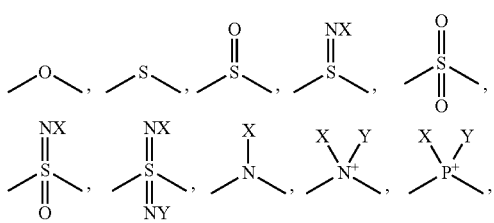

-continued

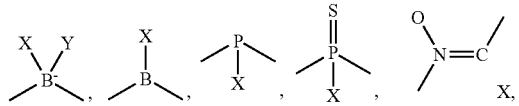

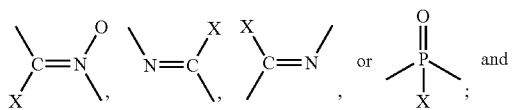

J is of the formula:

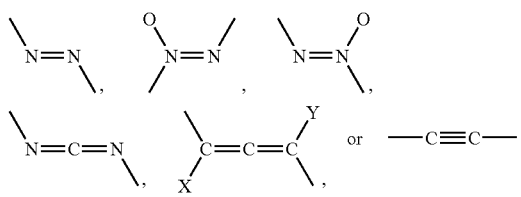

wherein:
A) each X and Y is independently a group of the formula:

-(L)$_m$-Z;

and

B) m is an integer from 0 to 8; and
C) no more than two E groups are adjacent to each other and no J groups are adjacent to each other;

iii) each Z is independently selected from:
A) hydrogen, halo, cyano, nitro, nitroso, azido, chlorate, bromate, iodate, isocyanato, isocyanido, isothiocyanato, pentafluorothio, or
B) a group G, wherein G is an unsubstituted or substituted; unsaturated, partially saturated, or saturated; monocyclic, bicyclic, tricyclic, or fused; carbocyclic or heterocyclic ring system wherein;
1) when the ring system contains a 3 or 4 membered heterocyclic ring, the heterocyclic ring contains 1 heteroatom;
2) when the ring system contains a 5, or more membered heterocyclic ring or a polycyclic heterocyclic ring, the heterocyclic or polycyclic heterocyclic ring contains from 1 to 4 heteroatoms;
3) each heteroatom is independently selected from N, O, and S;
4) the number of substituents is from 0 to 5 and each substituent is independently selected from X b) the total number of non-hydrogen atoms in each compound is 50 or less;

its enantiomers, stereoisomers, salts, and mixtures thereof; or a composition thereof.

2. A method of inhibiting an ethylene response in a plant, comprising contacting the plant with an effective ethylene response-inhibiting amount of a compound of formula III:

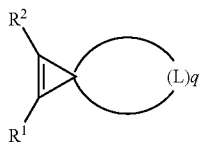

wherein:
a) each $R^1$ and $R^2$ is independently a group of the formula:

wherein:
i) n is an integer from 0 to 12 and q is an integer from 2 to 11;
ii) each L is independently selected from a member of group D, E, or J wherein:
    D is of the formula:

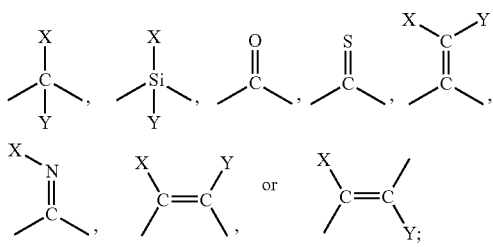

E is of the formula:

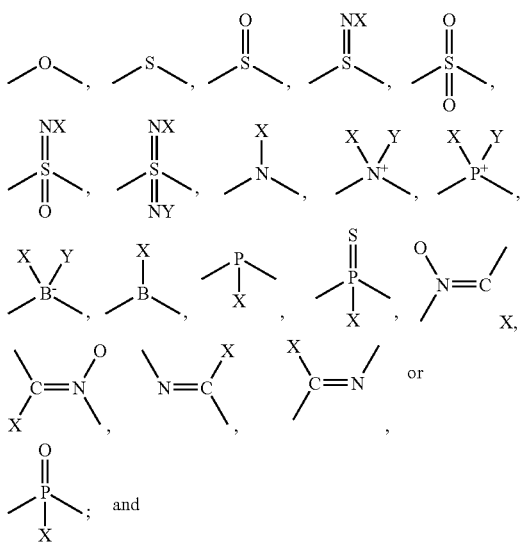

J is of the formula:

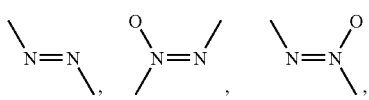

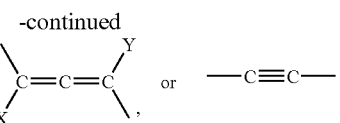

wherein:
A) each X and Y is independently a group of the formula:

and
B) m is an integer from 0 to 8; and
C) no more than two E groups are adjacent to each other and no J groups are adjacent to each other; and
iii) each Z is independently selected from:
    A) hydrogen, halo, cyano, nitro, nitroso, azido, chlorate, bromate, iodate, isocyanato, isocyanido, isothiocyanato, pentafluorothio, or
    B) a group G, wherein G is an unsubstituted or substituted; unsaturated, partially saturated, or saturated; monocyclic, bicyclic, tricyclic, or fused; carbocyclic or heterocyclic ring system wherein;
        1) when the ring system contains a 3 or 4 membered heterocyclic ring, the heterocyclic ring contains 1 heteroatom;
        2) when the ring system contains a 5, or more membered heterocyclic ring or a polycyclic heterocyclic ring, the heterocyclic or polycyclic heterocyclic ring contains from 1 to 4 heteroatoms;
        3) each heteroatom is independently selected from N, O, and S;
        4) the number of substituents is from 0 to 5 and each substituent is independently selected from X
b) the total number of non-hydrogen atoms in each compound is 50 or less;
its enantiomers, stereoisomers, salts, and mixtures thereof; or a composition thereof.

3. The method of claim 1 or claim 2, wherein the ethylene response is one or more of ripening or senescence of flowers, fruits, and vegetables; abscission of foliage, flowers, and fruit; the shortening of life of ornamental plants, cut flowers, shrubbery, seeds, or dormant seedlings; inhibition of growth; stimulation of growth; auxin activity; inhibition of terminal growth; control of apical dominance; increase in branching; increase in tillering; changing the morphology of plants, modifying the susceptibility to plant pathogens such as fungi; changing bio-chemical compositions; inducing pest resistance; abortion or inhibition of flowering or seed development; lodging effects; stimulation of seed germination; breaking of dormancy; hormone effects; and epinasty effects.

4. The method of claim 1, wherein the compound is of formula I and one of $R^3$ and $R^4$ is hydrogen.

5. The method of claim 1, wherein the compound is of formula II and one of $R^2$ and $R^3$ is hydrogen.

6. The method of claim 2, wherein one of $R^1$ and $R^2$ is hydrogen.

7. The method of claim 1 or claim 2, wherein n is from 0 to 8.

8. The method of claim 1 or claim 2, wherein m is from 0 to 4.

9. The method of claim 1, wherein p is from 4 to 7.

10. The method of claim 2, wherein q is from 4 to 6.

11. The method of claim 1 or claim 2, wherein:
a) each D is independently —CXY—, —SiXY—, —CO—, or —CS—;
b) each E is independently —O—, —S—, —NX—, or —$SO_2$—;
c) each X and Y is independently H, halo, OH, SH, —C(O)($C_1$–$C_4$)alkyl-, —C(O)O($C_1$–$C_4$)alkyl-, —O—($C_1$–$C_4$)alkyl, —S—($C_1$–$C_4$)alkyl, or substituted or unsubstituted ($C_1$–$C_4$)alkyl; and
d) each Z is independently H, halo, or G.

12. The method of claim 1 or claim 2, wherein $R^2$, $R^3$, and $R^4$, when present, are each independently selected from hydrogen and ($C_1$–$C_4$)alkyl.

* * * * *